(12) United States Patent
van der Weide et al.

(10) Patent No.: US 8,672,932 B2
(45) Date of Patent: Mar. 18, 2014

(54) CENTER FED DIPOLE FOR USE WITH TISSUE ABLATION SYSTEMS, DEVICES AND METHODS

(75) Inventors: Daniel W. van der Weide, Madison, WI (US); Fred T. Lee, Jr., Madison, WI (US); Paul F. Laeseke, Madison, WI (US); Christopher L. Brace, Madison, WI (US)

(73) Assignee: Neuwave Medical, Inc., Madison, WI (US)

( * ) Notice: Subject to any disclaimer, the term of this patent is extended or adjusted under 35 U.S.C. 154(b) by 739 days.

(21) Appl. No.: 11/728,457

(22) Filed: Mar. 26, 2007

(65) Prior Publication Data

US 2007/0282319 A1 Dec. 6, 2007

Related U.S. Application Data

(60) Provisional application No. 60/785,690, filed on Mar. 24, 2006.

(51) Int. Cl.
*A61B 18/18* (2006.01)

(52) U.S. Cl.
USPC ............................................. 606/33; 607/156

(58) Field of Classification Search
USPC ............... 606/32–50; 607/101–102, 154–156
See application file for complete search history.

(56) References Cited

U.S. PATENT DOCUMENTS

| 3,800,552 | A | 4/1974 | Sollami |
|---|---|---|---|
| 3,838,242 | A | 9/1974 | Goucher |
| 3,991,770 | A | 11/1976 | LeVeen |
| 4,057,064 | A | 11/1977 | Morrison |
| 4,074,718 | A | 2/1978 | Morrison |
| 4,312,364 | A | 1/1982 | Convert |
| 4,375,220 | A | 3/1983 | Matvias |
| 4,446,874 | A | 5/1984 | Vaguine |
| 4,494,539 | A | 1/1985 | Zenitani |
| 4,534,347 | A | 8/1985 | Taylor |
| 4,557,272 | A | 12/1985 | Carr |
| 4,589,424 | A | 5/1986 | Vaguine |
| 4,621,642 | A | 11/1986 | Chen |

(Continued)

FOREIGN PATENT DOCUMENTS

| EP | 1186274 | 3/2002 |
|---|---|---|
| EP | 1395190 | 3/2004 |

(Continued)

OTHER PUBLICATIONS

Golio, "The RF and microwave handbook" Edition: 2. Published by CRC Press, 2001 ISBN 0849338592X, 97808493859626.

(Continued)

*Primary Examiner* — Michael Peffley
*Assistant Examiner* — Daniel Fowler
(74) *Attorney, Agent, or Firm* — Casimir Jones SC

(57) ABSTRACT

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy employing a center fed dipole component. In certain embodiments, methods are provided for treating a tissue region (e.g., a tumor) through application of energy with the systems and devices of the present invention.

23 Claims, 2 Drawing Sheets

(56) References Cited

U.S. PATENT DOCUMENTS

| | | | |
|---|---|---|---|
| 4,627,435 A | 12/1986 | Hoskin | |
| 4,641,649 A | 2/1987 | Walinsky | |
| 4,643,186 A | 2/1987 | Rosen | |
| 4,662,383 A | 5/1987 | Sogawa | |
| 4,700,716 A | 10/1987 | Kasevich | |
| 4,712,559 A | 12/1987 | Turner | |
| 4,776,086 A | 10/1988 | Kasevich | |
| 4,790,311 A | 12/1988 | Ruiz | |
| 4,901,719 A | 2/1990 | Trenconsky | |
| 4,945,912 A | 8/1990 | Langberg | |
| 5,026,959 A | 6/1991 | Ito et al. | |
| 5,057,104 A | 10/1991 | Chess | |
| 5,057,106 A | 10/1991 | Kasevich | |
| 5,074,861 A | 12/1991 | Schneider | |
| RE33,791 E | 1/1992 | Carr | |
| 5,098,429 A | 3/1992 | Sterzer | |
| 5,129,396 A | 7/1992 | Rosen | |
| 5,150,717 A | 9/1992 | Rosen | |
| 5,167,619 A | 12/1992 | Wuchinich | |
| 5,211,625 A | 5/1993 | Sakurai | |
| 5,246,438 A | 9/1993 | Langberg | |
| 5,248,312 A | 9/1993 | Langberg | |
| 5,275,597 A | 1/1994 | Higgins | |
| 5,277,201 A | 1/1994 | Stern | |
| 5,281,213 A | 1/1994 | Milder | |
| 5,281,217 A | 1/1994 | Edwards | |
| 5,295,955 A * | 3/1994 | Rosen et al. | 604/22 |
| 5,300,099 A * | 4/1994 | Rudie | 607/101 |
| 5,301,687 A | 4/1994 | Wong | |
| 5,314,466 A | 5/1994 | Stern | |
| 5,344,418 A | 9/1994 | Ghaffari | |
| 5,344,435 A | 9/1994 | Turner | |
| 5,348,554 A | 9/1994 | Imran | |
| 5,358,515 A | 10/1994 | Hurter | |
| 5,364,392 A * | 11/1994 | Warner et al. | 606/34 |
| 5,366,490 A | 11/1994 | Edwards | |
| 5,369,251 A | 11/1994 | King | |
| 5,370,678 A | 12/1994 | Edwards | |
| 5,405,346 A | 4/1995 | Grundy | |
| 5,431,649 A | 7/1995 | Muller | |
| 5,433,740 A | 7/1995 | Yamaguchi | |
| 5,456,684 A * | 10/1995 | Schmidt et al. | 606/41 |
| 5,462,556 A | 10/1995 | Powers | |
| 5,472,423 A | 12/1995 | Gronauer | |
| 5,480,417 A | 1/1996 | Hascoet | |
| 5,496,271 A * | 3/1996 | Burton et al. | 607/27 |
| 5,507,743 A | 4/1996 | Edwards | |
| 5,531,677 A | 7/1996 | Lundquist | |
| 5,575,794 A | 11/1996 | Walus | |
| 5,578,029 A * | 11/1996 | Trelles et al. | 606/25 |
| 5,591,227 A | 1/1997 | Dinh | |
| 5,599,295 A | 2/1997 | Rosen | |
| 5,599,352 A | 2/1997 | Dinh | |
| 5,603,697 A | 2/1997 | Grundy et al. | |
| 5,620,479 A | 4/1997 | Diederich | |
| 5,647,871 A | 7/1997 | Levine | |
| 5,693,082 A | 12/1997 | Warner | |
| 5,697,949 A | 12/1997 | Giurtino | |
| 5,716,389 A | 2/1998 | Walinsky | |
| 5,737,384 A | 4/1998 | Fenn | |
| 5,741,249 A | 4/1998 | Moss | |
| 5,755,752 A | 5/1998 | Segal | |
| 5,755,754 A | 5/1998 | Rudie | |
| 5,759,200 A | 6/1998 | Azar | |
| 5,776,129 A | 7/1998 | Mersch | |
| 5,776,176 A | 7/1998 | Rudie | |
| 5,782,827 A | 7/1998 | Gough | |
| 5,788,692 A | 8/1998 | Campbell | |
| 5,788,694 A | 8/1998 | Vancaillie | |
| 5,800,494 A | 9/1998 | Campbell | |
| 5,810,803 A | 9/1998 | Moss | |
| 5,810,804 A | 9/1998 | Gough | |
| 5,849,029 A | 12/1998 | Eckhouse | |
| 5,902,251 A | 5/1999 | Vanhooydonk | |
| 5,921,935 A | 7/1999 | Hickey | |
| 5,957,969 A | 9/1999 | Warner | |
| 5,963,082 A | 10/1999 | Dick | |
| 5,995,875 A | 11/1999 | Blewett | |
| 6,002,968 A | 12/1999 | Edwards | |
| 6,012,457 A | 1/2000 | Lesh | |
| 6,016,811 A | 1/2000 | Knopp | |
| 6,026,331 A | 2/2000 | Feldberg | |
| 6,044,846 A | 4/2000 | Edwards | |
| 6,056,744 A | 5/2000 | Edwards | |
| 6,067,475 A | 5/2000 | Graves | |
| 6,073,052 A | 6/2000 | Zelickson | |
| 6,083,255 A | 7/2000 | Laufer | |
| 6,097,985 A | 8/2000 | Zasevich | |
| 6,102,885 A * | 8/2000 | Bass | 604/22 |
| 6,104,959 A | 8/2000 | Spertell | |
| 6,106,524 A | 8/2000 | Eggers | |
| 6,188,930 B1 | 2/2001 | Carson | |
| 6,190,382 B1 | 2/2001 | Ormsby | |
| 6,208,903 B1 | 3/2001 | Richards | |
| 6,223,085 B1 | 4/2001 | Dann | |
| 6,230,060 B1 | 5/2001 | Mawhinney | |
| 6,235,022 B1 | 5/2001 | Hallock et al. | |
| 6,245,062 B1 | 6/2001 | Berube | |
| 6,251,128 B1 | 6/2001 | Knopp | |
| 6,254,598 B1 | 7/2001 | Edwards | |
| 6,273,884 B1 | 8/2001 | Altshuler | |
| 6,273,885 B1 | 8/2001 | Koop | |
| 6,277,113 B1 | 8/2001 | Berube | |
| 6,287,302 B1 | 9/2001 | Berube | |
| 6,306,130 B1 | 10/2001 | Anderson | |
| 6,306,132 B1 * | 10/2001 | Moorman et al. | 606/41 |
| 6,312,427 B1 | 11/2001 | Berube | |
| 6,325,796 B1 | 12/2001 | Berube | |
| 6,347,251 B1 | 2/2002 | Deng | |
| 6,355,033 B1 | 3/2002 | Moorman | |
| 6,364,876 B1 | 4/2002 | Erb | |
| 6,383,182 B1 | 5/2002 | Berube | |
| 6,395,803 B1 | 5/2002 | Angeletakis | |
| 6,398,781 B1 | 6/2002 | Goble | |
| 6,427,089 B1 | 7/2002 | Knowlton | |
| 6,435,872 B1 | 8/2002 | Nagel | |
| 6,471,696 B1 | 10/2002 | Berube | |
| 6,485,486 B1 * | 11/2002 | Trembly et al. | 606/33 |
| 6,500,174 B1 | 12/2002 | Maguire | |
| 6,506,189 B1 | 1/2003 | Rittman | |
| 6,514,249 B1 | 2/2003 | Maguire | |
| 6,524,308 B1 | 2/2003 | Muller | |
| 6,527,768 B2 | 3/2003 | Berube | |
| 6,546,077 B2 | 4/2003 | Chornenky | |
| 6,575,969 B1 | 6/2003 | Rittman, III | |
| 6,577,903 B1 | 6/2003 | Cronin | |
| 6,582,426 B2 | 6/2003 | Moorman | |
| 6,582,486 B1 | 6/2003 | Delpiano | |
| 6,585,733 B2 | 7/2003 | Wellman | |
| 6,593,395 B2 | 7/2003 | Angeletakis | |
| 6,602,074 B1 | 8/2003 | Suh | |
| 6,622,731 B2 | 9/2003 | Daniel | |
| 6,635,055 B1 | 10/2003 | Cronin | |
| 6,652,520 B2 | 11/2003 | Moorman | |
| 6,663,625 B1 | 12/2003 | Ormsby | |
| 6,673,068 B1 | 1/2004 | Berube | |
| 6,702,576 B2 | 3/2004 | Fischer | |
| 6,709,271 B2 | 3/2004 | Yin | |
| 6,740,107 B2 | 5/2004 | Leob | |
| 6,749,606 B2 | 6/2004 | Keast | |
| 6,752,767 B2 | 6/2004 | Turovskiy | |
| D493,531 S | 7/2004 | Padain | |
| 6,770,070 B1 | 8/2004 | Balbierz | |
| 6,780,178 B2 | 8/2004 | Palanker | |
| 6,802,840 B2 | 10/2004 | Chin | |
| 6,817,976 B2 | 11/2004 | Rovegno | |
| 6,817,999 B2 | 11/2004 | Berube | |
| 6,823,218 B2 | 11/2004 | Berube | |
| 6,837,712 B2 | 1/2005 | Qian | |
| 6,847,848 B2 | 1/2005 | Sterzer | |
| 6,849,075 B2 | 2/2005 | Bertolero et al. | |
| 6,852,091 B2 | 2/2005 | Edwards | |
| 6,866,624 B2 | 3/2005 | Chornenky | |
| 6,866,663 B2 | 3/2005 | Edwards | |

(56) References Cited

U.S. PATENT DOCUMENTS

| | | | |
|---|---|---|---|
| 6,869,431 | B2 | 3/2005 | Maguire |
| 6,878,147 | B2 | 4/2005 | Prakash |
| 6,890,968 | B2 | 5/2005 | Angeletakis |
| 6,893,436 | B2 | 5/2005 | Woodard |
| 6,898,454 | B2 | 5/2005 | Atalar |
| D507,649 | S | 7/2005 | Padain |
| 6,918,905 | B2 | 7/2005 | Neuberger |
| 6,924,325 | B2 | 8/2005 | Qian |
| 6,957,108 | B2 | 10/2005 | Turner |
| 6,962,586 | B2 | 11/2005 | Berube |
| 6,972,016 | B2 | 12/2005 | Hill |
| 6,976,986 | B2 | 12/2005 | Berube |
| 6,994,546 | B2 | 2/2006 | Fischer |
| 7,022,105 | B1 | 4/2006 | Edwards |
| 7,033,352 | B1 | 4/2006 | Gauthier |
| 7,101,369 | B2 | 9/2006 | van der Welde |
| 7,147,632 | B2 | 12/2006 | Prakash |
| 7,153,298 | B1 | 12/2006 | Cohen |
| 7,156,842 | B2 | 1/2007 | Sartor et al. |
| 7,160,289 | B2 | 1/2007 | Cohen |
| 7,160,292 | B2 | 1/2007 | Moorman |
| 7,184,824 | B2 | 2/2007 | Hashimshony |
| 7,197,363 | B2 | 3/2007 | Prakash |
| 7,244,254 | B2 | 7/2007 | Brace |
| 7,266,407 | B2 | 9/2007 | Li |
| 7,311,703 | B2 | 12/2007 | Turovskiy |
| 7,318,824 | B2 | 1/2008 | Prakash |
| 7,331,960 | B2 | 2/2008 | Schaer |
| 7,381,208 | B2 | 6/2008 | van der Walt |
| 7,400,929 | B2 | 7/2008 | Zelickson et al. |
| 7,467,015 | B2 | 12/2008 | van der Weide et al. |
| 7,601,149 | B2 | 10/2009 | DiCarlo et al. |
| 7,722,620 | B2 | 5/2010 | Truckai |
| 7,826,904 | B2 | 11/2010 | Appling |
| 2002/0022836 | A1 | 2/2002 | Goble |
| 2002/0087151 | A1 | 7/2002 | Mody |
| 2002/0173780 | A1 | 11/2002 | Altshuler |
| 2003/0060813 | A1 | 3/2003 | Loeb |
| 2003/0065317 | A1 | 4/2003 | Rudie |
| 2004/0082859 | A1 | 4/2004 | Schaer |
| 2004/0116921 | A1 | 6/2004 | Sherman |
| 2004/0158237 | A1 | 8/2004 | Abboud |
| 2004/0267248 | A1 | 12/2004 | Duong |
| 2005/0011885 | A1 | 1/2005 | Seghatol |
| 2005/0075629 | A1 | 4/2005 | Chapelon |
| 2005/0107870 | A1 | 5/2005 | Wang |
| 2005/0143726 | A1 | 6/2005 | Bortkiewicz |
| 2005/0149010 | A1 | 7/2005 | Turovskiy |
| 2005/0165389 | A1 | 7/2005 | Swain |
| 2005/0245920 | A1 | 11/2005 | Vitullo et al. |
| 2006/0155270 | A1 | 7/2006 | Hancock |
| 2006/0264921 | A1 | 11/2006 | Deutsch et al. |
| 2007/0282319 | A1 | 12/2007 | van der Weide |
| 2007/0288079 | A1 | 12/2007 | van der Weide |
| 2008/0033424 | A1 | 2/2008 | Van der Weide |
| 2008/0147056 | A1 | 6/2008 | Van der Weide |

FOREIGN PATENT DOCUMENTS

| | | | |
|---|---|---|---|
| EP | | 1450710 | 9/2004 |
| EP | | 1499251 | 1/2005 |
| EP | | 1542607 | 6/2005 |
| EP | | 1723922 | 11/2006 |
| GB | | 2388039 | 11/2003 |
| GB | | 2406521 | 4/2005 |
| WO | | 92/04934 | 4/1992 |
| WO | | 9309845 | 5/1993 |
| WO | | 9504385 | 9/1995 |
| WO | | 9748449 | 12/1997 |
| WO | WO | 9748449 | * 12/1997 |
| WO | | 99/56643 | 11/1999 |
| WO | | 00/57811 | 10/2000 |
| WO | | 03/039385 | 5/2003 |
| WO | | 03/088806 | 10/2003 |
| WO | | 03/088858 | 10/2003 |
| WO | | 2004/004586 | 1/2004 |
| WO | | 2004026122 | 1/2004 |
| WO | | 2004/033039 | 4/2004 |
| WO | | 2004/112628 | 12/2004 |
| WO | | 2005/034783 | 4/2005 |
| WO | | 2005/110265 | 11/2005 |
| WO | | 2006/002943 | 1/2006 |
| WO | | 2006/005579 | 1/2006 |
| WO | | 2006/008481 | 1/2006 |
| WO | | 2008/142686 | 11/2008 |
| WO | | 2011/008903 | 1/2011 |
| WO | | 2011/140087 | 11/2011 |

OTHER PUBLICATIONS

International Search Report, PCT/US2006/017981, dated Sep. 7, 2006.

International Search Report, PCT/US2006/033341, dated Aug. 17, 2007.

International Search Report, PCT/US06/032811, dated Jan. 25, 2007.

International Search Report, PCT/US06/031644, dated Aug. 17, 2007.

International Search Report, PCT/US2006/028821, dated Mar. 21, 2007.

International Search Report, PCT/US2005/014534, dated Nov. 29, 2005.

Brace, Christopher et al., "Analysis and experimental validation of a triaxial antenna for microwave tumor ablation," IEEE MTTS Int Microw Symp. Jun. 3, 2004 (6-11), 1437-1440.

Brace, Christopher et al., "Microwave Ablation with a Triaxial Antenna: Results in ex vivo Bovine Liver," IEEE Transations on Microwave Theory and Techniques, vol. 53, No. 1 Jan. 2005.

Seki, Toshihito, et al., "Ultrasonically Guided Percutaneous Microwave Coagulation Therapy for Small Hepatocellular Carcinoma," Cancer, Aug. 1, 1994, vol. 74, No. 3, pp. 817-825.

Head, Hayden W., et al., "Thermal Ablation for Hepatocellular Carcinoma," Gastroenterology, 2004:127:S167-S178.

* cited by examiner

CENTER FED DIPOLE FOR USE WITH TISSUE ABLATION SYSTEMS, DEVICES AND METHODS

This application claims priority to U.S. Provisional Application Ser. No. 60/785,690, filed Mar. 24, 2006, herein incorporated by reference in its entirety.

FIELD OF THE INVENTION

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy employing a center fed dipole component. In certain embodiments, methods are provided for treating a tissue region (e.g., a tumor) through application of energy with the systems and devices of the present invention.

BACKGROUND

Ablation is an important therapeutic strategy for treating certain tissues such as benign and malignant tumors, cardiac arrhythmias, cardiac dysrhythmias and tachycardia. Most approved ablation systems utilize radiofrequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641,649, 5,246,438, 5,405,346, 5,314,466, 5,800,494, 5,957,969, 6,471,696, 6,878,147, and 6,962,586; each of which is herein incorporated by reference in their entireties).

Unfortunately, current devices configured to deliver microwave energy have drawbacks. For example, current devices produce relatively small lesions because of practical limits in power and treatment time. Current devices have power limitations in that the power carrying capacity of the feedlines are small. Larger diameter feedlines are undesirable, however, because they are less easily inserted percutaneously and may increase procedural complication rates. In addition, heating of the feedline at high powers can lead to burns around the area of insertion for the device.

Improved systems and devices for delivering energy to a tissue region are needed. In addition, improved systems and devices capable of delivering sufficient amounts of microwave energy without corresponding microwave energy loss are needed. In addition, systems and devices capable of percutaneous delivery of microwave energy to a subject's tissue without undesired tissue burning or invasive damage are needed. Furthermore, systems for delivery of desired amounts of microwave energy without requiring physically large invasive components are needed.

SUMMARY OF THE INVENTION

The present invention relates to systems and devices for delivering energy to tissue for a wide variety of applications, including medical procedures (e.g., tissue ablation, resection, cautery, vascular thrombosis, intraluminal ablation of a hollow viscus, cardiac ablation for treatment of arrhythmias, electrosurgery, tissue harvest, cosmetic surgery, intraocular use, etc.). In particular, the present invention relates to systems and devices for the delivery of energy employing a center fed dipole component. In certain embodiments, methods are provided for treating a tissue region (e.g., a tumor) through application of energy with the systems and devices of the present invention.

In some embodiments, the present invention provides a device having therein a center fed dipole for heating a tissue region through application of energy (e.g., microwave energy). The devices of the present invention are not limited to a particular design configuration. In preferred embodiments, the devices of the present invention have a coaxial cable connected to a hollow tube (e.g., where the interior diameter is at least 50% of the exterior diameter; e.g., where the interior diameter is substantially similar to the exterior diameter). The coaxial cable may be a standard coaxial cable, or it may be a coaxial cable having therein a dielectric component with a near-zero conductivity (e.g., air). The hollow tube is not limited to a particular design configuration. In preferred embodiments, the hollow tube assumes the shape of (e.g., diameter of), for example, a 20-gauge needle. Preferably, the hollow tube is made of a solid, rigid conductive material (e.g., any number of metals, conductor-coated ceramics or polymers, etc.). In some embodiments, the hollow tube is configured with a sharpened point or the addition of a stylet on its distal end to permit direct insertion of the device into a tissue region without the use of, for example, a cannula. The hollow tube is not limited to a particular composition (e.g., metal, plastic, ceramic). In some embodiments, the hollow tube comprises, for example, copper or copper alloys with other hardening metals, silver or silver alloys with other hardening metals, gold-plated copper, metal-plated Macor (machinable ceramic), metal-plated hardened polymers, and/or combinations thereof.

The present invention is not limited by the manner in which the hollow tube is connected to the coaxial cable. In some embodiments, a portion of the outer conductor at the distal end of the coaxial cable feedline is removed, exposing a region of solid dielectric material. The hollow tube can be positioned onto the exposed dielectric material and attached by any means. In some preferred embodiments, a physical gap between the outer conductor and the hollow tube is provided. In some preferred embodiments, the hollow tube is capacitively or conductively attached to the feedline at its center point such that the electrical length of the hollow tube comprises a frequency-resonant structure when inserted into tissue.

In use, the devices are configured such that an electric field maximum is generated at the open distal end of the hollow tube. In some embodiments, the distal end of the hollow tube has a pointed shape so as to assist in inserting the device though a subject and into a tissue region. In some embodiments, the entire device is hard and rigid so as to facilitate linear and direct insertion directly to a target site. In some embodiments, the structure resonates at, for example, ~2.45 GHz, as characterized by a minimum in the reflection coefficient (measured at the proximal end of the feedline) at this frequency. By changing the dimensions of the device (e.g., length, feed point, diameter, gap, etc.) and materials (dielectric materials, conductors, etc.) of the antenna, the resonant frequency may be changed. A low reflection coefficient at a desired frequency ensures efficient transmission of energy from the antenna to the medium surrounding it.

Preferably, the hollow tube is of length $\lambda/2$, where $\lambda$ is the electromagnetic field wavelength in the medium of interest (e.g., ~18 cm for 2.45 GHz in liver) to resonate within the medium. In some embodiments, the length of the hollow tube is approximately $\lambda/2$, where $\lambda$ is the electromagnetic field wavelength in the medium of interest to resonate within the medium, such that a minimum of power reflection at the proximal end is measured. However, deviations from this length may be employed to generate resonant wavelengths (e.g., as the surrounding materials are changed). Preferably, the inner conductor of a coaxial cable is extended with its distal end at the tube center (e.g., at $\lambda/4$ from the end of the tube) and configured such that the inner conductor maintains electrical contact at the tube center, although deviations from this position are permitted (e.g., to generate resonant wavelengths).

The devices are configured for mounting in various medical devices, intravascular delivery devices, surgical cutting instruments (e.g., having blades), surgical cautery instruments, flexible catheters, inflexible catheters, and general surgical instruments and accessories. For example, in some embodiments, the devices may be mounted in a flexible catheter or other intravascular delivery devices for purposes of, for example, cardiac ablation to treat arrhythmias, or intravascular ablation for treatment of varicose veins, vascular aneurysms, or arterio-venous malformations. In some embodiments, the devices may be incorporated into or associate with a device with a sharp, cutting edge or other cutting mechanism to allow for simultaneous cutting and coagulating of tissue.

The hollow tube portion of the present invention may have a wide variety of shapes. In some embodiments, the tube is cylindrical throughout its length. In some embodiments, tube tapers from a center position such that it has a smaller diameter at its end as compared to its center. Having a smaller point at the distal end assists in penetrating a subject to arrive at the target region. In preferred embodiments, where the shape of the hollow tube deviates from a cylindrical shape, the tube maintains a symmetrical structure on either side of its longitudinal center. However, the present invention is not limited by the shape of the hollow tube, so long as the functional properties are achieved (i.e., the ability to deliver desired energy to a target region).

The present invention contemplates that the center-fed dipole components of the invention may be added to the distal end of a wide variety of ablation devices to provide the benefits described herein. Likewise, a wide variety of devices may be modified to accept the center-fed dipole components of the present invention.

In certain embodiments, the present invention provides a center fed dipole device comprising an antenna configured for delivery of energy to a tissue, wherein the device comprises a coaxial cable and a hollow tube, the coaxial cable having a dielectric material disposed between an inner conductor and an outer conductor, wherein the inner conductor extends into the hollow tube. The device is not limited to a particular type of energy (e.g., microwave energy, radiofrequency energy). In some embodiments, the hollow tube has a diameter equal to or less than, for example, a 20-gauge needle, a 17-gauge needle, or a 12-gauge needle, although higher gauge and smaller gauge needles are further contemplated. In some embodiments, the device is configured to deliver a sufficient amount of energy to ablate the tissue region or cause thrombosis. In some embodiments, the inner conductor extends halfway through the hollow tube. In some embodiments, the device further comprises a tuning element for adjusting the amount of energy delivered to the tissue region.

In certain embodiments, the present invention provides a system for ablation therapy, comprising a center fed dipole device, and for example, a power distributor, a generator, surgical accessories, software, etc.

In certain embodiments, the present invention provides a method of treating a tissue region, comprising providing a tissue region and a center fed dipole device, positioning the device in the vicinity of the tissue region, and delivering an amount of energy with the device to the tissue region (e.g., a tumor, heart, blood vessel).

The present invention is not limited by the type of device or the uses employed. Indeed, the devices may be configured in any desired manner. Likewise, the systems and devices may be used in any application where energy is to be delivered. Such uses include any and all medical, veterinary, and research applications. However, the systems and devices of the present invention may be used in agricultural settings, manufacturing settings, mechanical settings, or any other application where energy is to be delivered.

The systems, devices, and methods of the present invention may further employ a wide range of additional features and components, including, but not limited to, flow of coolants (e.g., gasses, liquids, mixtures thereof, etc.) though one or more portions of the device to manage temperature within or around the device; sensors; coatings; and the like.

In some embodiments, the device is configured for percutaneous, intravascular, intracardiac, laparoscopic, or surgical delivery of energy. In some embodiments, the device is configured for delivery of energy to a target tissue or region. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, and cauterization of blood vessels or tissue for any purposes. In some embodiments, the surgical application comprises ablation therapy (e.g., to achieve coagulation necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the device is configured for guided delivery, for example, by computerized tomography, ultrasound, magnetic resonance imaging, fluoroscopy, and the like.

The device is not limited to a particular shape or size of the components that deliver energy to the target tissue. In some embodiments, the outer conductor or component with the greatest diameter that enters the subject is a 20-gauge needle or a component of similar diameter to a 20-gauge needle. Preferably, the outer diameter is not larger than a 16-gauge needle (e.g., no larger than an 18-gauge needle). In some embodiments, the outer diameter is not larger than a 17-gauge needle. However, in some embodiments, larger devices are used, as desired. For example, in some embodiments, a 12-gauge diameter is used. The present invention is not limited by the size of the components. In preferred embodiments, some or all of the feedline characteristic impedance is optimized for minimum power dissipation, irrespective of the type of antenna that terminates its distal end. In some embodiments, the device has therein multiple antenna arrays of the same or different shapes (e.g., umbrella-shaped probes, trident shaped, etc.).

The some embodiments, the systems of the present invention provide multiple feedlines and/or multiple antennas to affect one or more locations in a subject, any one or more of which can comprise a center-fed dipole component of the present invention. Such application include, but are not limited to, treating large tumor masses or tumor masses having irregular shapes, where one or more of the components capable of delivered energy is inserted to a first position of a tumor and one or more of the components is inserted to a second (third, etc.) position of a tumor. In some embodiments, a first component capable of delivering energy is a first size and a second component capable of delivery energy is a second size. Such an embodiment, adds to the choices a user has in delivering the desired amount of energy for a particular application. For example, in embodiments where the size of the injury created by insertion of the device into a subject is less relevant and the tissue zone to be ablated is larger, the user may select a larger needle to deliver more energy. In contrast, where the injury associated with the insertion is to be minimized, two or more smaller needles may be used (e.g., bundled together or separately).

In some embodiments, one or more components of the systems of the present invention may contain a coating (e.g., Teflon or any other insulator) to help reduce heating or to impart other desired properties to the component or system.

In some embodiments, the device further comprises a tuning element for adjusting the amount of energy delivered to the tissue region. In some embodiments, the tuning element is manually adjusted by a user of the system. In some embodiments, the device is pretuned to the desired tissue and is fixed throughout the procedure. In some embodiments, the tuning element is automatically adjusted and controlled by a processor of the present invention. In some embodiments, the processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

In certain embodiments, the present invention provides systems for ablation therapy, comprising a power distributor and a device of the present invention for percutaneous delivery of energy to a tissue region. In some embodiments, the power distributor includes a power splitter configured to deliver energy to multiple antennas (e.g., the same energy power to each antenna, different energy powers to different antennas). In some embodiments, the power splitter is able to receive power from one or more power distributors.

In certain embodiments, the present invention provides methods for treating a tissue region, comprising providing a target tissue or organism and a device of the present invention for delivery of energy to a tissue region. In such embodiments, the method further comprises the positioning of the device in the vicinity of the tissue region, and the percutaneous delivering of an amount of energy with the device to the tissue region. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord.

The systems, devices, and methods of the present invention may be used in conjunction with other systems, device, and methods. For example, the systems, devices, and methods of the present invention may be used with other ablation devices, other medical devices, diagnostic methods and reagents, imaging methods and reagents, and therapeutic methods and agents. Use may be concurrent or may occur before or after another intervention. The present invention contemplates the use systems, devices, and methods of the present invention in conjunction with any other medical interventions.

DETAILED DESCRIPTION

Figure 1:
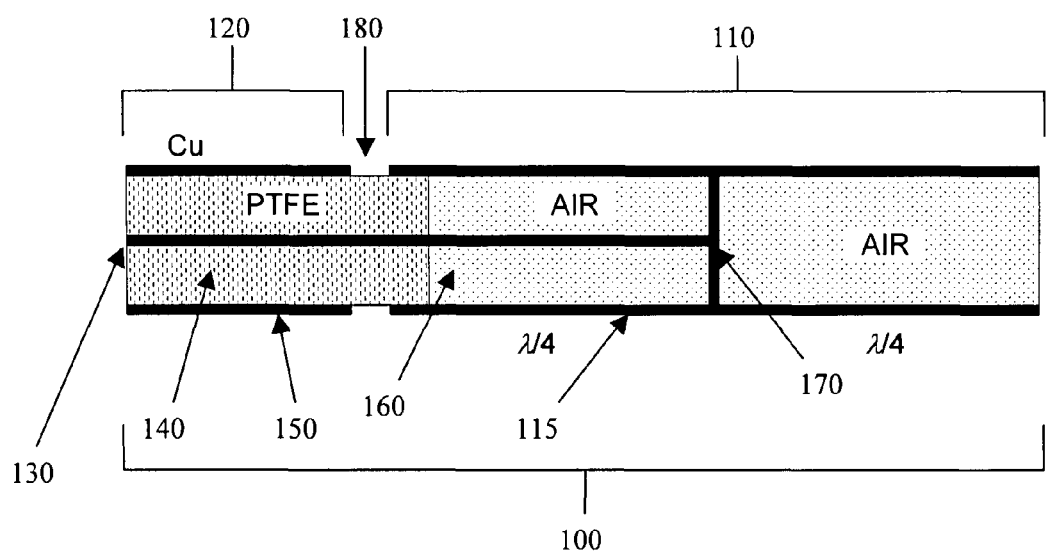
FIG. 1 schematically shows a center fed dipole device.

The present invention relates to systems and devices for delivering energy to tissue for a wide variety of applications, including medical procedures (e.g., tissue ablation, treatment of arrhythmias, cautery, vascular thrombosis, electrosurgery, tissue harvest, etc.). In particular, the present invention relates to systems and devices for the delivery of energy employing a center fed dipole component. In certain embodiments, methods are provided for treating a tissue region (e.g., a tumor) through application of energy with the systems and devices of the present invention.

In preferred embodiments, the systems, devices, and methods of the present invention employ microwave energy. The use of microwave energy in the ablation of tissue has numerous advantages. For example, microwaves have a broad field of power density (e.g., approximately 2 cm surrounding an antenna depending on the wavelength of the applied energy) with a correspondingly large zone of active heating, thereby allowing uniform tissue ablation both within a targeted zone and in perivascular regions (see, e.g., International Publication No. WO 2006/004585; herein incorporated by reference in its entirety). In addition, microwave energy has the ability to ablate large or multiple zones of tissue using multiple probes with more rapid tissue heating. Microwave energy has an ability to penetrate tissue to create deep lesions with less surface heating. Energy delivery times are shorter than with radiofrequency energy and probes can heat tissue sufficiently to create an even and symmetrical lesion of predictable and controllable depth. Microwave energy is generally safe when used near vessels. Also, microwaves do not rely on electrical conduction; they can radiate through tissue, fluid/blood, as well as air. Therefore, they can be used in tissue, lumins, lungs, and intravascularly.

The illustrated embodiments provided below describe the systems and devices of the present invention in terms of medical applications (e.g., ablation of tissue through delivery of microwave energy). However, it should be appreciated that the systems and devices of the present invention are not limited to a medical applications. In addition, the illustrated embodiments describe the systems and devices of the present invention in terms of medical devices configured for tissue ablation. It should be appreciated that the systems and devices of the present invention are not limited to medical devices configured for tissue ablation. The illustrated embodiments describe the systems and devices of the present invention in terms of microwave energy. It should be appreciated that the systems and devices of the present invention are not limited to a particular type of energy (e.g., radiofrequency energy).

In some embodiments, the devices of the present invention have a small outer diameter. In some preferred embodiments, the center-fed dipole component of the invention is directly used to insert the invasive component of the device into a subject. In some such embodiments, the device does not contain a cannula, allowing for the invasive components to have a smaller outer diameter. For example, the invasive component can be designed such that it fits within or is the size of very small needles (e.g., 18-20 gauge needles or smaller). Typically, medical devices configured to deliver microwave energy are designed to fit within large needles due to bulky dielectric materials. Microwave ablation has not been extensively applied clinically due to the large probe size (14 gauge) and relatively small zone of necrosis (1.6 cm in diameter) (Seki T et al., Cancer 74:817 (1994)) that is created by the only commercial device (Microtaze, Nippon Shoji, Osaka, Japan. 2.450 MHz, 1.6 mm diameter probe, 70 W for 60 seconds). Other devices use a cooling external water jacket that also increases probe size and can increase tissue damage. These large probe sizes increase the risk of complications when used in the chest and abdomen. In some embodiments of the present invention, the maximum outer diameter of the portion of the device that enters a subject is 16-18 gauge or less (20 gauge or less).

Certain preferred embodiments of the present invention are described below. The present invention is not limited to these embodiments.

FIG. 1 schematically shows the distal end of a device 100 (e.g., antenna of an ablation device) of the present invention that comprises a center fed dipole component 110 of the present invention. One skilled in the art will appreciate any number of alternative configurations that accomplish the physical and/or functional aspects of the present invention. As shown, the center fed dipole device 100 has therein a hollow tube 115 and a coaxial transmission line 120 (e.g., a coaxial cable). The center fed dipole device 100 is not limited to a particular size. In preferred embodiments, the size of the center fed dipole device 100 is small enough to be positioned at a tissue region (e.g., a liver) for purposes of delivering energy (e.g., microwave energy) to that tissue region.

Referring again to FIG. 1, the hollow tube 115 is not limited to a particular material (e.g., plastic, ceramic, metal, etc.). The hollow tube 115 is not limited to a particular length. In some embodiments, the length. of the hollow tube is $\lambda/2$, where $\lambda$ is the electromagnetic field wavelength in the medium of interest (e.g., ~18 cm for 2.45 GHz in liver). The hollow tube 115 engages the coaxial transmission line 120 such that the hollow tube 115 is attached to the coaxial transmission line 120 (described in more detail below). The hollow tube 115 has therein a hollow tube matter 160. The hollow tube 115 is not limited to a particular type of hollow tube matter. In some embodiments, the hollow tube matter 160 is air, fluid or a gas.

Still referring to FIG. 1, the hollow tube 115 is not limited to a particular shape (e.g., cylindrical, triangular, squared, rectangular, etc.). In some embodiments, the shape of the hollow tube 115 is of a needle (e.g., a 20-gauge needle, an 18-gauge needle). In some embodiments, the hollow tube 115 is divided into two portions each of equal length (e.g., each portion having a length of $\lambda/4$). In such embodiments, the shapes of each portion are symmetrical. In some embodiments, the hollow tube has a diameter equal to or less than a 20-gauge needle, a 17-gauge needle, a 12-gauge needle, etc.

Still referring to FIG. 1, the coaxial transmission line 120 is not limited to a particular type of material. In some embodiments, the proximal coaxial transmission line 120 is constructed from commercial-standard 0.047-inch semi-rigid coaxial cable. In some embodiments, the coaxial transmission line 120 is metal-plated (e.g., silver-plated, copper-plated), although the present invention is not so limited. The proximal coaxial transmission line 120 is not limited to a particular length.

Still referring to FIG. 1, in some embodiments, the coaxial transmission line 120 has a coaxial center conductor 130, a coaxial dielectric material 140, and a coaxial outer conductor 150. In some embodiments, the coaxial center conductor 130 is configured to conduct cooling fluid along its length. In some embodiments, the coaxial center conductor 130 is hollow. In some embodiments, the coaxial center conductor 130 has a diameter of, for example, 0.012 inches. In some embodiments, the coaxial dielectric material 140 is polyfluorotetraethylene (PTFE). In some embodiments, the coaxial dielectric material 140 has a near-zero conductivity (e.g., air, fluid, gas).

Still referring to FIG. 1, the distal end of the coaxial transmission line 120 is configured to engage the proximal end of the hollow tube 115. In some embodiments, the coaxial center conductor 130 and the coaxial dielectric material 140 extend into the center of the hollow tube 115. In some embodiments, the coaxial center conductor 120 extends further into the hollow tube 115 than the coaxial dielectric material 140. The coaxial center conductor 120 is not limited to a particular amount of extension into the hollow tube 115. In some embodiments, the coaxial center conductor 120 extends a length of $\lambda/4$ into the hollow tube 115. The distal end of the coaxial transmission line 120 is not limited to a particular manner of engaging the proximal end of the hollow tube 115. In some embodiments, the proximal end of the hollow tube engages the coaxial dielectric material 140 so as to secure the hollow tube 115 with the coaxial transmission line 120. In some embodiments, the distal end of the coaxial center conductor engages the walls of the hollow tube 115 directly or though contact with a connecting material 170, which may be made of the same material as the coaxial center conductor or may be of a different material (e.g., a different conductive material).

Still referring to FIG. 1, in some embodiments, a gap 180 exists between the distal end of the coaxial transmission line outer conductor 150 and the hollow tube 115 thereby exposing the coaxial dielectric material 140. The gap 180 is not limited to a particular size or length. In some embodiments, the gap 180 ensures an electric field maximum at the proximal end of the coaxial transmission line 180 and the distal open end of the hollow tube 115. In some embodiments, the center fed dipole device 110 resonates at ~2.45 GHz, as characterized by a minimum in the reflection coefficient at this frequency. By changing the dimensions (length, feed point, diameter, gap, etc.) and materials (dielectric materials, conductors, etc.) of the device the resonant frequency may be changed. A low reflection coefficient at this frequency ensures efficient transmission of energy from the antenna to the medium surrounding it.

Figure 2:
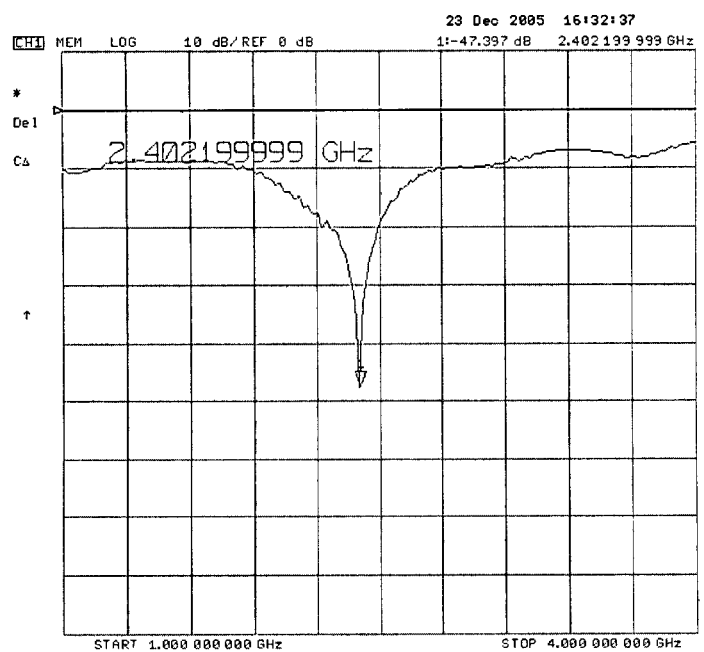
FIG. 2 shows a graph of the reflection coefficient minimum for a center fed dipole device.

For example, FIG. 2 shows the reflection coefficient measured using a microwave network analyzer, and showing a minimum of −47.4 dB for a center fed dipole device of the present invention in ex vivo bovine liver. This indicates that the device of the present invention is tuned for minimum power reflection in the tissue of interest. By changing the overall length of the hollow tube, the point at which the feedline is connected to the hollow tube, and the materials used in connecting the hollow tube to the feedline, different resonant frequencies are observed. In this manner, the devices of the present invention can be tuned to minimize or nearly minimum power reflection and hence maximum power delivery to tissue.

The systems and devices of the present invention may be combined within various system/kit embodiments. For example, the present invention provides kits comprising one or more of a generator, a power distribution system, and a center fed dipole device, along with any one or more accessory agents (e.g., surgical instruments, software for assisting in procedure, processors, temperature monitoring devices, etc.). The present invention is not limited to any particular accessory agent. Additionally, the present invention contemplates kits comprising instructions (e.g., ablation instructions, pharmaceutical instructions) along with the systems and devices of the present invention and/or a pharmaceutical agent (e.g., a sedating medication, a topical antiseptic, a topical anesthesia).

The devices of the present invention may be used in any medical procedure (e.g., percutaneous or surgical) involving delivery of energy (e.g., microwave energy) to a tissue region. The present invention is not limited to a particular type or kind of tissue region (e.g., brain, liver, heart, blood vessels, foot, lung, bone, etc.). For example, the systems of the present invention find use in ablating tumor regions. In such uses, the center fed dipole device is inserted into, for example, a subject such that the distal end of the hollow tube is positioned in the vicinity of the desired tissue region. Next, a generator is used to provide a desired amount of microwave energy to a power distribution system at a characteristic impedance level, which in turn provides the energy at a characteristic impedance level to the center fed dipole device. Next, a desired amount of energy is delivered to the desired tissue region (e.g., tumor) generating an electric field of sufficient strength to ablate the desired tissue region. The present invention further provides methods involving the simultaneous use of multiple (e.g., two or more) applicator devices for the treatment of a tissue. In some embodiments, the present invention provides methods wherein the simultaneous use of multiple antennas are phased to achieve constructive and destructive interference (e.g., for purposes of selectively destroying and sparing portions of a tissue region).

In some embodiments, the present invention further provides software for regulating the amount of energy (e.g., microwave energy) provided to a tissue region through monitoring of the temperature of the tissue region (e.g., through a feedback system). In such embodiments, the software is configured to interact with the systems for microwave therapy of the present invention such that it is able to raise or lower (e.g., tune) the amount of energy delivered to a tissue region. In some embodiments, the type of tissue being treated (e.g., liver) is inputted into the software for purposes of allowing the software to regulate (e.g., tune) the delivery of microwave energy to the tissue region based upon pre-calibrated methods for that particular type of tissue region. In other embodiments, the software provides a chart or diagram based upon a particular type of tissue region displaying characteristics useful to a user of the system. In some embodiments, the software provides energy delivering algorithms for purposes of, for example, slowly ramping power to avoid tissue cracking due to rapid out-gassing created by high temperatures. In some embodiments, the software allows a user to choose power, duration of treatment, different treatment algorithms for different tissue types, simultaneous application of power to the antennas in multiple antenna mode, switched power delivery between antennas, coherent and incoherent phasing, etc.

In some embodiments, the software is configured for imaging equipment (e.g., CT, MRI, ultrasound). In some embodiments, the imaging equipment software allows a user to make predictions based upon known thermodynamic and electrical properties of tissue and location of the antenna(s). In some embodiments, the imaging software allows the generation of a three-dimensional map of the location of a tissue region (e.g., tumor, arrhythmia), location of the antenna(s), and to generate a predicted map of the ablation zone.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A device comprising an antenna configured for delivery of energy to a tissue, wherein a distal end of said antenna comprises a center-fed dipole component comprising a rigid hollow tube encompassing a conductor, wherein said conductor has a proximal end and a distal end, wherein said distal end of said conductor engages said rigid hollow tube via connection with the center of a conductive material that spans across said rigid hollow tube thereby preventing said distal end of said conductor from contact with said rigid hollow tube, wherein said distal end of said conductor does not extend beyond said conductive material thereby preventing said conductor from contact with said tissue, wherein said hollow tube has a diameter equal to or less than a 16-gauge needle, wherein said energy is microwave energy.

2. The device of claim 1, wherein said hollow tube has a diameter equal to or less than a 20-gauge needle.

3. The device of claim 1, wherein said hollow tube has a diameter equal to or less than a 17-gauge needle.

4. The device of claim 1, further comprising a tuning element for adjusting the amount of energy delivered to said tissue.

5. The device of claim 1, wherein said device is configured to deliver a sufficient amount of energy to ablate said tissue or cause thrombosis.

6. The device of claim 1, wherein said conductor extends halfway through said hollow tube.

7. The device of claim 1, wherein said hollow tube has a length of approximately $\lambda/2$, wherein $\lambda$ is the electromagnetic field wavelength in the medium of the tissue to resonate within the medium, such that a minimum of power reflection at the proximal end is provided.

8. A system for ablation therapy, comprising a power distributor and a device comprising an antenna configured for delivery of energy to a tissue, wherein a distal end of said antenna comprises a center-fed dipole component comprising a rigid hollow tube encompassing a conductor, wherein said conductor has a proximal end and a distal end, wherein said distal end of said conductor engages said rigid hollow tube via connection with the center of a conductive material that spans across said rigid hollow tube thereby preventing said distal end of said conductor from contact with said rigid hollow tube, wherein said distal end of said conductor does not extend beyond said conductive material thereby preventing said conductor from contact with said tissue, said hollow tube has a diameter equal to or less than a 16-gauge needle, wherein said energy is microwave energy.

9. The device of claim 8, wherein said hollow tube has a diameter equal to or less than a 20-gauge needle.

10. The system of claim 8, wherein said hollow tube has a diameter equal to or less than a 17-gauge needle.

11. The system of claim 8, further comprising a tuning element for adjusting the amount of energy delivered to said tissue.

12. The system of claim 8, wherein said device is configured to deliver a sufficient amount of energy to ablate said tissue or cause thrombosis.

13. The system of claim 8, wherein said inner conductor extends halfway through said hollow tube.

14. The device of claim 8, wherein said hollow tube has a length $\lambda/2$, wherein $\lambda$ is the electromagnetic field wavelength in the medium of the tissue to resonate within the medium, such that a minimum of power reflection at the proximal end is provided.

15. The system of claim 8, further comprising a generator.

16. A method of treating a tissue region, comprising:
a) providing a tissue region and a device comprising an antenna configured for delivery of energy to a tissue, wherein a distal end of said antenna comprises a center-fed dipole component comprising a rigid hollow tube encompassing a conductor, wherein said conductor has a proximal end and a distal end, wherein said distal end of said conductor engages said rigid hollow tube via connection with the center of a conductive material that spans across said rigid hollow tube thereby preventing said distal end of said conductor from contact with said rigid hollow tube, wherein said distal end of said conductor does not extend beyond said conductive material thereby preventing said conductor from contact with said tissue, wherein said hollow tube has a diameter equal to or less than a 16-gauge needle, wherein said energy is microwave energy;
b) positioning said device in the vicinity of said tissue region,
c) delivering an amount of energy with said device to said tissue region.

17. The method of claim 16, wherein said tissue region is a tumor.

18. The device of claim 16, wherein said hollow tube has a diameter equal to or less than a 20-gauge needle.

19. The method of claim 16, wherein said hollow tube has a diameter equal to or less than a 17-gauge needle.

20. The method of claim 16, further providing a tuning element for adjusting the amount of energy delivered to said tissue region.

21. The method of claim 16, wherein said device is configured to deliver a sufficient amount of energy to ablate said tissue region or cause thrombosis.

22. The method of claim 16, wherein said inner conductor extends halfway through said hollow tube.

23. The method of claim 16, wherein said hollow tube has a length of approximately $\lambda/2$, wherein $\lambda$ is the electromagnetic field wavelength in the medium of the tissue to resonate within the medium, such that a minimum of power reflection at the proximal end is provided.

* * * * *